United States Patent [19]
Midha et al.

[11] Patent Number: 6,113,883
[45] Date of Patent: Sep. 5, 2000

[54] HAIR STYLING COMPOSITIONS COMPRISING SILICONE-CONTAINING COPOLYMERS

[75] Inventors: Sanjeev Midha, Blue Ash; Raymond Edward Bolich, Jr., Maineville; Kathleen Bridget Jividen, Lebanon, all of Ohio

[73] Assignee: The Procter & Gamble Company, Cincinnati, Ohio

[21] Appl. No.: 08/939,362

[22] Filed: Sep. 29, 1997

Related U.S. Application Data

[63] Continuation-in-part of application No. 08/842,938, Apr. 25, 1997, abandoned.

[51] Int. Cl.[7] .............................. A61K 9/00; A61K 7/11; A61K 31/695
[52] U.S. Cl. ......................... 424/47; 424/45; 424/70.11; 424/70.12; 424/DIG. 1; 424/DIG. 2; 514/63; 514/957
[58] Field of Search ............................... 528/30; 514/957, 514/63; 526/279; 525/301, 370; 424/47, 45, 70.11, DIG. 1, DIG. 2, 70.12

[56] References Cited

U.S. PATENT DOCUMENTS

| | | | |
|---|---|---|---|
| 4,724,851 | 2/1988 | Cornwall et al. | 132/7 |
| 4,728,571 | 3/1988 | Clemens et al. | 428/352 |
| 4,733,677 | 3/1988 | Gee et al. | 132/7 |
| 4,744,978 | 5/1988 | Homan et al. | 424/70 |
| 4,749,565 | 6/1988 | Grollier | 424/70 |
| 4,814,402 | 3/1989 | Nakashima et al. | 526/245 |
| 4,902,499 | 2/1990 | Bolich, Jr. et al. | 424/70 |
| 4,933,176 | 6/1990 | van Reeth | 424/70 |
| 4,963,595 | 10/1990 | Ward et al. | 525/415 |
| 4,972,037 | 11/1990 | Garbe et al. | 526/245 |
| 4,981,902 | 1/1991 | Mitra et al. | 524/547 |
| 4,981,903 | 1/1991 | Garbe et al. | 524/547 |
| 4,983,377 | 1/1991 | Murphy et al. | 424/47 |
| 4,988,506 | 1/1991 | Mitra et al. | 424/81 |
| 5,002,762 | 3/1991 | Bolich, Jr. | 424/70 |
| 5,021,477 | 6/1991 | Garbe et al. | 424/70 |

(List continued on next page.)

FOREIGN PATENT DOCUMENTS

| | | | |
|---|---|---|---|
| 18835 | 1/1993 | Australia . | |
| 18835/92 | 6/1996 | Australia | A61K 7/032 |
| 0 117 360 A1 | 9/1984 | European Pat. Off. | C08L 83/08 |
| 0 408 311 A2 | 1/1991 | European Pat. Off. | C08F 230/08 |
| 0 766 957 A1 | 4/1997 | European Pat. Off. | A61K 7/06 |
| 4-359912 | 12/1992 | Japan | C08F 299/08 |
| 4-359913 | 12/1992 | Japan | C08F 299/08 |
| 4-360812 | 12/1992 | Japan | A61K 7/100 |
| 88/05060 | 7/1988 | WIPO | C08F 30/08 |
| 93/23009 | 11/1993 | WIPO | A61K 7/48 |
| 95/03776 | 2/1995 | WIPO | A61K 7/06 |
| 95/04518 | 2/1995 | WIPO | A61K 7/06 |
| 95/06079 | 3/1995 | WIPO | C08G 77/42 |
| 96/32918 | 10/1996 | WIPO | A61K 7/06 |

*Primary Examiner*—Thurman K. Page
*Assistant Examiner*—Brian K. Seidleck
*Attorney, Agent, or Firm*—William J. Winter; Andrew A Paul

[57] ABSTRACT

The present invention relates to hair styling compositions and in particular to hair spray compositions. These compositions comprise a silicone containing adhesive copolymer, having a weight average molecular weight from about 10,000 to about 5,000,000, and a solvent for said copolymer selected from the group consisting of water, ethanol, n-propanol, isopropanol, and mixtures thereof. The spray compositions, when dried, have a cohesive strength of greater than about 0.5 kgf/mm$^2$, a total energy absorption per unit volume of greater than about 0.55 kgfmm/mm$^3$ and , preferably an impact strength of greater than about 7000 ergs. The hairspray embodiments of the present invention preferably provide improved removeability from hair as defined by a hair stiffness value of from 0 to about 3.5 (0 to 4 scale) and a hair flaking value of from 0 to about 3.5 (0 to 4 scale) as determined by the removeability methodology defined herein. The instant invention also relates to a method of styling and/or holding hair comprising the step of applying to the hair an effective amount of the above compositions.

24 Claims, 1 Drawing Sheet

U.S. PATENT DOCUMENTS

| | | | |
|---|---|---|---|
| 5,061,481 | 10/1991 | Suzuki et al. | 424/63 |
| 5,100,658 | 3/1992 | Bolich, Jr. et al. | 424/70 |
| 5,104,646 | 4/1992 | Bolich, Jr. et al. | 424/70 |
| 5,106,609 | 4/1992 | Bolich, Jr. et al. | 424/70 |
| 5,115,049 | 5/1992 | Imperante et al. | 525/479 |
| 5,120,812 | 6/1992 | O'Lenick, Jr. et al. | 528/28 |
| 5,166,276 | 11/1992 | Hayama et al. | 525/329.7 |
| 5,209,924 | 5/1993 | Garbe et al. | 424/71 |
| 5,219,560 | 6/1993 | Suzuki et al. | 424/63 |
| 5,229,435 | 7/1993 | Sakai et al. | 523/105 |
| 5,258,490 | 11/1993 | Chang | 528/488 |
| 5,294,437 | 3/1994 | Shah et al. | 424/70.11 |
| 5,468,477 | 11/1995 | Kumar et al. . | |
| 5,523,365 | 6/1996 | Geck et al. | 526/194 |
| 5,565,193 | 10/1996 | Midha et al. | 424/70.12 |
| 5,618,524 | 4/1997 | Bolich, Jr. et al. | 424/70.12 |
| 5,620,684 | 4/1997 | Dupuis | 424/70.12 |
| 5,622,694 | 4/1997 | Torgerson et al. | 424/70.122 |
| 5,632,998 | 5/1997 | Midha et al. | 424/401 |
| 5,653,968 | 8/1997 | Carballada et al. | 424/70.11 |
| 5,653,969 | 8/1997 | Carballada et al. | 424/70.16 |
| 5,658,552 | 8/1997 | Bunning et al. | 424/47 |
| 5,658,557 | 8/1997 | Bolich, Jr. et al. | 424/70.12 |
| 5,662,892 | 9/1997 | Bolich, Jr. et al. | 424/70.1 |
| 5,665,337 | 9/1997 | Carballada et al. | 424/70.12 |
| 5,667,771 | 9/1997 | Carballada et al. | 424/70.12 |
| 5,725,882 | 3/1998 | Kumar et al. . | |
| 5,730,966 | 3/1998 | Torgerson et al. | 424/70.11 |
| 5,753,216 | 5/1998 | Leitch et al. | 424/70.12 |
| 5,763,548 | 6/1998 | Matyjaszewski et al. | 526/135 |
| 5,807,937 | 9/1998 | Matyjaszewski et al. | 526/135 |
| 5,830,477 | 11/1998 | Hutchins et al. . | |
| 5,843,881 | 12/1998 | Dubois et al. . | |
| 5,911,979 | 6/1999 | Midha et al. . | |
| 5,916,548 | 6/1999 | Hutchins et al. . | |
| 5,919,879 | 7/1999 | Midha et al. . | |
| 5,929,173 | 7/1999 | Midha et al. . | |
| 5,986,015 | 11/1999 | Midha et al. . | |

HAIR STYLING COMPOSITIONS COMPRISING SILICONE-CONTAINING COPOLYMERS

This application is a continuation-in-part of Ser. No. 08/842,938, filed on Apr. 25, 1997, now abandoned.

TECHNICAL FIELD

The present invention relates to hair styling compositions including hair spray compositions, especially hair spray compositions having improved removeability from hair as defined by hair stiffness and flaking values. These spray compositions provide good style retention characteristics without being stiff or sticky. These compositions comprise a silicone containing adhesive copolymer and a solvent for the copolymer selected from the group consisting of water, ethanol, n-propanol, isopropanol, and mixtures thereof. The spray compositions, when dried, exhibit a cohesive strength of greater than about 0.5 kgf/mm$^2$, and a total energy absorption per unit volume of greater than about 0.55 kgfmm/mm$^3$. The compositions, when dried, also preferably exhibit an impact strength of greater than about 7000 ergs.

BACKGROUND OF THE INVENTION

The desire to have the hair retain a particular style or shape is widely held. The most common methodology for accomplishing this is by spraying a composition, typically from a mechanical pump spray device or from a pressurized aerosol canister, to the hair. Such compositions provide temporary setting benefits and can usually be removed by water or by shampooing. The materials used in hair spray compositions are generally resins, gums, and adhesive polymers.

Many people desire a high level of style retention, or hold, from a hair spray composition. Most current hair spray compositions have disadvantages. Spray products that have good hold characteristics tend to be either too stiff or too sticky upon drying. Stiff compositions tend to be brittle and break down under common stresses such as wind, brushing, combing. Stiff compositions also tend to feel and look unnatural. Sticky compositions overcome many of the foregoing disadvantages of stiff compositions, because, sticky compositions tend to be more forgiving, i.e. flexible, under stress and allow for restyling of the hair. However, sticky compositions have the disadvantage of leaving the hair with a heavy, coated feel and with a limp and unattractive appearance. Also, sticky compositions cause the hair to quickly become soiled from common contaminant sources such as dust, dirt, lint, sebum, etc. Therefore, a need exists for hair spray compositions providing good style retention without the disadvantages of stiff or sticky compositions.

Surprisingly, the present invention provides hair spray compositions having good style retention without being stiff or sticky. The resulting hair styles obtained from using these compositions hold up well under the common stress conditions and other factors as mentioned above. Importantly, such compositions provide the benefit of allowing the user to restyle the hair without the need for reapplication of spray product. The spray compositions of the present invention leave the hair both feeling and looking natural. Also, these products do not have the disadvantage of causing the hair to quickly resoil.

Because of growing environmental awareness among consumers, there is also a desire for hair spray compositions having reduced volatile organic compound (i.e. "VOC") levels. Typically, reduced VOC hair sprays have 80% or less of VOCs, whereas conventional VOC hair sprays have greater than about 80% of VOCs. In certain embodiments, the hair spray compositions of the present invention can be formulated as reduced VOC hair sprays.

The compositions of the present invention provide the recited benefits by utilizing certain silicone containing adhesive copolymers in combination with a solvent for the copolymer selected from the group consisting of water, ethanol, n-propanol, isopropanol, and mixtures thereof. These spray compositions, when dried, have a cohesive strength of greater than about 0.5 kgf/mm$^2$, a total energy absorption per unit volume of greater than about 0.55 kgfmm/mm$^3$, and preferably an impact strength of greater than about 7000 ergs. Without being limited by theory, it is believed that these physical characteristics of the dried hair spray composition account for the benefits observed.

It has also been found that the preferred hair spray compositions of the present invention have an improved removeability from hair during shampooing, wherein the removeability is defined in terms of hair stiffness and hair flaking values ranging from 0 to about 3.5 (0 to 4 scale). These hair stiffness and flaking values are indirect measures of hair spray removeability. Each of these values are determined in accordance with the methodology defined herein.

It is therefore an object of this invention to provide hair styling compositions, and especially hair spray compositions, that provide improved hair style retention or hold without leaving the hair stiff or sticky.

It is another object of this invention to provide hair spray compositions that both look and feel natural.

It is another object of this invention to provide hair spray compositions that meet the requirement for conventional VOC levels, as well as for reduced VOC levels.

It is another object of this invention to provide methods for styling and holding hair.

These and other objects will become readily apparent from the detailed description which follows.

SUMMARY OF THE INVENTION

The present invention relates to hair styling compositions, especially hair spray compositions, comprising:
 (a) a silicone-containing adhesive copolymer having a weight average molecular weight from about 10,000 to about 5,000,000, and
 (b) a solvent for said copolymer selected from the group consisting of water, ethanol, n-propanol, isopropanol, and mixtures thereof,
wherein said hair spray composition, when dried, has a cohesive strength of greater than about 0.5 kgf/mm$^2$ and a total energy absorption per unit volume of greater than about 0.55 kgfmm/mm$^3$. The hair spray compositions also preferably have improved removeability, wherein removeability is defined by a hair stiffness value of from 0 to about 3.5 and a hair flaking value of from 0 to 3.5 (0 to 4 scale).

In further embodiments, the present invention relates to hair spray compositions wherein the hair spray composition, when dried, has an impact strength of greater than about 7000 ergs.

In further embodiments, the present invention relates to a method of styling and/or holding hair comprising the step of applying to the hair an effective amount of a composition comprising,
 (a) a silicone-containing adhesive copolymer having a weight average molecular weight from about 10,000 to about 5,000,000, and (b) a solvent for said copolymer selected from the group consisting of water, ethanol, n-propanol, isopropanol, and mixtures thereof, wherein said hair spray composition, when dried, has a cohesive strength of greater than about 0.5 kgf/mm$^2$ and a total energy absorption per unit volume of greater than about 0.55 kgfmm/mm$^3$.

DETAILED DESCRIPTION OF THE INVENTION

The essential components of the present invention are described below. Also included is a nonexclusive description of various optional and preferred components useful in embodiments of the present invention.

The present invention can comprise, consist of, or consist essentially of any of the required or optional ingredients and/or limitations described herein.

All percentages and ratios are calculated on a weight basis unless otherwise indicated. All percentages are calculated based upon the total composition unless otherwise indicated.

All molecular weights are weight average molecular weights and are given in units of grams per mole.

All ingredient levels are in reference to the active level of that ingredient, and are exclusive of solvents, by-products, or other impurities that may be present in commercially available sources, unless otherwise indicated.

All measurements made are at ambient room temperature, which is approximately 73° F., unless otherwise designated.

All documents referred to herein, including all patents, patent applications, and printed publications, are hereby incorporated by reference in their entirety in this disclosure.

The term "suitable for application to human hair" as used herein, means that the compositions or components thereof so described are suitable for use in contact with human hair and the scalp and skin without undue toxicity, incompatibility, instability, allergic response, and the like.

The term kgf is a standard physical term denoting a kilogram of force subjected to gravitational acceleration, i.e. 9.82 m/s$^2$.

SILICONE-CONTAINING ADHESIVE COPOLYMER

The compositions of the present invention comprise from about 0.1% to about 30%, preferably from about 0.5% to about 20%, and more preferably from about 0.5% to about 10%, by weight of the composition, of a silicone-containing adhesive copolymer.

By "adhesive" is meant that when applied as a solution to a surface and dried, e.g., the hair fibers, the copolymer forms films or welds. Such a film or weld will have adhesive and cohesive strength, as is understood by those skilled in the art.

By "silicone-containing" is meant that the copolymers contain one or more alkyl or aryl siloxane moieties, as defined further in the specification.

The copolymers of the present invention are selected from the group consisting of silicone grafted copolymers, silicone block copolymers, sulfur-linked silicone containing copolymers, sulfur-linked silicone block copolymers, and mixtures thereof.

The term "silicone grafted copolymers" is familiar to one of ordinary skill in polymer science and is used herein to describe the copolymers which result by adding or "grafting" polymeric silicone moieties (i.e. "grafts") onto another polymeric moiety commonly referred to as the "backbone". The backbone typically has a higher molecular weight than the grafts. Thus, silicone grafted copolymers can be described as polymers having pendant polymeric silicone side chains, and as being formed from the "grafting" or incorporation of polymeric silicone side chains onto or into a polymer backbone. The polymer backbone can be a homopolymer or a copolymer. The graft copolymers are derived from a variety of monomer units. Additionally, these copolymers can comprise grafts derived from nonsilicone-containing macromonomers, e.g., macromonomers formed by the polymerization of acrylates, methacrylates, and other ethylenic moieties. These macromonomers can be selected to have either high (>25° C.) or low $T_g$ ($\leq 25°$ C.) values. The term Tg means glass transition temperature, which is familiar to one of ordinary skill in polymer science.

The term "block copolymers" is familiar to one of ordinary skill in polymer science and is used herein to describe copolymers having sequentially arranged moieties or blocks which are further composed of smaller repeating units. The block copolymers herein comprise silicone blocks and non-silicone blocks. The block copolymers can be represented by the following structures: A-B structures, containing two block segments; A-B-A, containing three block segments, and -(A-B)$_n$-, wherein n is an integer of 2 or greater, containing multiple blocks.

The term "sulfur-linked" as used herein in the terms "sulfur-linked silicone grafted copolymer" and "sulfur-linked silicone block copolymer" means a silicone grafted or block copolymer containing a sulfur linkage (i.e. —S—), a disulfide linkage (i.e. —S—S—), or a sulfhydryl group (i.e. —SH).

The copolymers, or salts thereof, of the present invention are soluble or dispersible in a solvent selected from the group consisting of water, ethanol, n-propanol, isopropanol, and mixtures thereof, at a concentration of at least about 0.1 mg/mL, preferably at least about 0.5 mg/mL, and more preferably at least about 1 mg/mL, at about 73° F.

The copolymers of the present invention have a weight average molecular weight, in grams/mole, of at least about 10,000. There is no upper limit for molecular weight except that which limits applicability of the invention for practical reasons, such as viscosity, processing, aesthetic characteristics, spreadability, formulation compatibility, etc. The weight average molecular weight is generally less than about 5,000,000, more generally less than about 2,500,000, and typically less than about 1,500,000. Preferably, the weight average molecular weight is from about 10,000 to about 5,000,000, more preferably from about 20,000 to about 1,000,000, even more preferably from about 30,000 to about 500,000, and most preferably from about 50,000 to about 300,000.

A wide variety of silicone containing adhesive copolymers are useful in the present invention, provided the physical parameters of the dried hair spray film and the solubility or dispersibility requirements and the molecular weight requirements of the copolymer are met.

SILICONE GRAFTED COPOLYMERS

The silicone-grafted copolymers of the present invention are formed from the random copolymerization of vinyl monomer units and polysiloxane-containing macromonomer units containing a polymeric portion and a vinyl moiety copolymerizable with vinyl monomer units. Upon completion of polymerization, the siloxane polymeric portion of the macromonomer units forms the polysiloxane side chains of the copolymer. The vinyl monomer units and the vinyl moiety portion of the macromonomer units from the backbone. The vinyl monomer and the polysiloxane-containing macromonomer can be selected form a wide variety of structures as long as the copolymer has the required properties described herein.

As will be clear to one skilled in the art, and especially from the Examples, the copolymer may have one or more polysiloxane side chains grafted to the backbone. In addition, the compositions of the present invention can include, in addition to the copolymer, low levels of the corresponding copolymers having no polysiloxane side chains grafted to the backbone. As known in the art, synthetic graft copolymerization processes may produce a mixture of polymer molecules containing none, one, or more than one polysiloxane side chains covalently bonded to and pendant from the polymeric backbone. From knowledge of the amount and number average molecular weight of side chains in a polymer sample, and the number average molecular weight of the polymer sample, it is possible to calculate the average number of polysiloxane side chains per polymer backbone.

The grafted copolymers should satisfy the following three criteria:

(1) when dried the copolymer phase-separates into a discontinuous phase which includes the grafted polymeric side chain portion and a continuous phase which includes the non-side chain portion;

(2) the polymeric side chain portion is covalently bonded to the backbone portion; and (3) the number average molecular weight of the polymeric side chain portion is from about 1000 to about 50,000.

Without being limited by theory, it is believed that the phase separation property provides a specific orientation of the copolymer which results in the desired combination of tactile feel, film-forming or adhesive benefits, and the ability to dry quickly and completely. The phase-separating nature of the compositions of the present invention may be determined as follows.

The copolymer is cast as a solid film out of a solvent as described below. This film is then sectioned and examined by transmission electron microscopy. Microphase separation is demonstrated by the observation of inclusions in the continuous phase. These inclusions should have the proper size to match the size of the side chains (typically a few hundred nm or less) and the proper density to match the amount of side chain present. This behavior is well documented in the literature for polymers with this structure. See, for example, S. D. Smith, Ph.D. Thesis, University of Virginia, 1987, and references cited therein, said thesis incorporated by reference herein.

The copolymers of the present invention are prepared by the polymerization combination of vinyl monomers and polysiloxane macromonomers. The copolymers can be synthesized by free radical polymerization of the monomers and macromonomers. The general principles of free radical polymerization methods are well understood. See, for example, Odian, "Principles of Polymerization", 3rd edition, John Wiley & Sons, 1991, pp. 198–334. The desired vinyl monomers and polysiloxane macromonomers are all placed in a reactor, along with a sufficient amount of a mutual solvent so that when the reaction is complete the viscosity of the reaction is reasonable. Undesired terminators, especially oxygen, are removed as needed. This is done by evacuation or by purging with an inert gas, such as argon or nitrogen. The initiator is introduced and the reaction brought to the temperature needed for initiation to occur, assuming thermal initiators are used. Alternatively, redox or radiation initiation can be used. The polymerization is allowed to proceed as long as needed for a high level of conversion to be achieved, typically from a few hours to a few days. The solvent is then removed, usually by evaporation or by precipitating the copolymer by addition of a nonsolvent. The copolymer can be further purified, as desired.

As an alternative to a batch reaction, the copolymer can be made by a semi-continuous or continuous process. In the semi-continuous process, two or more additions of monomers or macromonomers are made during the polymerization reaction. This is advantageous when the copolymer is made of several monomers which react during the polymerization at different rates. The proportions of monomers added to the reaction at the separate points of addition can be adjusted by one of ordinary skill in the art such that the polymers of the final product have a more uniform structure. In other words, the polymers of the final product will have a more consistent monomer content distribution for each of the monomer types charged to the reaction.

Examples of related copolymers and how they are made are described in detail in U.S. Pat. No. 4,693,935, Mazurek, issued Sep. 15, 1987, U.S. Pat. No. 4,728,571, Clemens et al., issued Mar. 1, 1988, both of which are incorporated herein by reference. Additional silicone grafted polymers are also disclosed in EPO Application 90307528.1, published as EPO Application 0 408 311 A2 on Jan. 11, 1991, Hayama, et al., U.S. Pat. No. 5,061,481, issued Oct. 29, 1991, Suzuki et al., U.S. Pat. No. 5,106,609, Bolich et al., issued Apr. 21, 1992, U.S. Pat. No. 5,100,658, Bolich et al., issued Mar. 31, 1992, U.S. Pat. No. 5,100,657, Ansher-Jackson, et al., issued Mar. 31, 1992, U.S. Pat. No. 5,104,646, Bolich et al., issued Apr. 14, 1992, U.S. Pat. No. 5,618,524 issued Apr. 8, 1997, Bolich et al, and U.S. Ser. No. 07/758,320, Torgerson et al., filed Aug. 27, 1991, abandoned, all of which are incorporated by reference herein in their entirety.

The copolymers are prepared by the polymerization combination of vinyl monomers and polysiloxane macromonomers. The copolymer composition is characterized by the amount of each monomer charged to the polymerization reaction vessel, or alternatively used in a continuous or semi-continuous process.

By appropriate selection and combination of the particular vinyl monomer units and polysiloxane macromonomer units, and by the choice of specific relative ratios of the units well within the ability of one of ordinary skill in the art, the copolymers can be optimized for various physical properties and for compatibility with other ingredients commonly used in hair care applications.

VINYL MONOMER UNITS

The silicone copolymers of the present invention comprise from about 50% to about 98%, preferably from about 60% to about 95%, and more preferably from about 70% to about 90% by weight of the vinyl monomer units.

The vinyl monomer unit is selected from copolymerizable monomers, preferably ethylenically unsaturated monomers. Either a single type of vinyl monomer unit or combinations of two or more vinyl monomer units can be utilized. The vinyl monomers are selected to meet the requirements of the copolymer. By "copolymerizable", as used herein, is meant that the vinyl monomer can be reacted with or polymerized with the polysiloxane macromonomers in a polymerization reaction using one or more conventional synthetic techniques, such as ionic, emulsion, dispersion, Ziegler-Natta, free radical, group transfer or step growth polymerization. In the present invention, monomers and macromonomers that are copolymerizable using conventional free radical initiated techniques are preferred. The term "ethylenically unsaturated" is used herein to mean a material that contains at least one polymerizable carbon-carbon double bond, which can be mono-, di-, tri- or tetra-substituted.

The monomer units can be derived from hydrophilic monomers (typically polar monomers), or mixtures of such hydrophilic monomers with hydrophobic monomers (typically low polarity monomers), provided that the solubility characteristics of the overall copolymer is achieved. As used herein, "hydrophilic monomers" means monomers which form homopolymers which are substantially water soluble; "hydrophobic monomers" means monomers which form substantially water insoluble homopolymers.

Nonlimiting classes of monomers useful herein include monomers selected from the group consisting of unsaturated alcohols, unsaturated monocarboxylic acids, unsaturated dicarboxylic acids, unsaturated anhydrides, alcohol esters of unsaturated monocarboxylic acids, alcohol esters of unsaturated dicarboxylic acids, alcohol esters of unsaturated anhydrides, alkoxylated esters of unsaturated monocarboxylic acids, alkoxylated esters of unsaturated dicarboxylic acids, alkoxylated esters of unsaturated anhydrides, aminoalkyl esters of unsaturated monocarboxylic acids, aminoalkyl esters of unsaturated dicarboxylic acids, aminoalkyl esters of unsaturated anhydrides, amides of unsaturated monocarboxylic acids, amides of unsaturated dicarboxylic acids, amides of unsaturated anhydrides, salts of unsaturated monocarboxylic acids, salts of unsaturated dicarboxylic acids, salts of unsaturated anhydrides, unsaturated hydrocarbons, unsaturated heterocycles, and mixtures thereof.

Representative examples of such monomers include acrylic acid, methacrylic acid, N,N-dimethylacrylamide, dimethylaminoethyl methacrylate, quaternized dimethylaminoethyl methacrylate, methacrylamide, N-t-butyl acrylamide, maleic acid, maleic anhydride and its half esters, crotonic acid, itaconic acid, acrylamide, acrylate alcohols, hydroxyethyl methacrylate, diallyldimethyl ammonium chloride, vinyl pyrrolidone, vinyl ethers (such as methyl vinyl ether), maleimides, vinyl pyridine, vinyl imidazole, other polar vinyl heterocyclics, styrene sulfonate, allyl alcohol, vinyl alcohol (such as that produced by the hydrolysis of vinyl acetate after polymerization), vinyl caprolactam, methacrylic acid esters of $C_1$–$C_{18}$ alcohols, such as methanol, ethanol, methoxy ethanol, 1-propanol, 2-propanol, 1-butanol, 2-methyl-1-propanol, 1-pentanol, 2-pentanol, 3-pentanol, 2-methyl-1-butanol, 1-methyl-1-butanol, 3-methyl-1-butanol, 1-methyl-1-pentanol, 2-methyl-1-pentanol, 3-methyl-1-pentanol, t-butanol(2-methyl-2-propanol), cyclohexanol, neodecanol, 2-ethyl-1-butanol, 3-heptanol, benzyl alcohol, 2-octanol, 6-methyl-1-heptanol, 2-ethyl-1-hexanol, 3,5-dimethyl-1-hexanol, 3,5,5-tri methyl-1-hexanol, 1-decanol, 1-dodecanol, 1-hexadecanol, 1-octa decanol, and the like, the alcohols having from about 1–18 carbon atoms with the number of carbon atoms preferably being from about 1–12; dicyclopentenyl acrylate; 4-biphenyl acrylate; pentachlorophenyl acrylate; 3,5-dimethyladamantyl acrylate; 3,5-dimethyladamentyl methacrylate; 4-methoxycarbonylphenyl methacrylate; trimethylsilyl methacrylate; styrene; alkyl substituted styrenes including alpha-methylstyrene and t-butylstyrene; vinyl esters, including vinyl acetate, vinyl neononanoate, vinyl pivalate and vinyl propionate; vinyl chloride; vinylidene chloride; vinyl toluene; alkyl vinyl ethers, including isobutyl vinyl ether and s-butyl vinyl ether; butadiene; cyclohexadiene; bicycloheptadiene; 2,3-dicarboxylmethyl-1,6-hexadiene; ethylene; propylene; indene; norbornylene; β-pinene; α-pinene; salts of acids and amines listed above, and combinations thereof. The quaternized monomers can be quaternized either before or after the copolymerization with other monomers of the graft copolymer.

Preferred monomers include acrylic acid, methacrylic acid, N,N-dimethyl acrylamide, dimethylaminoethyl methacrylate, quaternized dimethylaminoethyl methacrylate, vinyl pyrrolidone, acrylic or methacrylic acid esters of $C_1$–$C_{18}$ alcohols, styrene, alpha-methylstyrene, t-butylstyrene, vinyl acetate, vinyl propionate, 2-methoxyethyl acrylate, 2-ethoxyethyl acrylate, n-butyl methacrylate, isobutyl methacrylate, t-butyl acrylate, t-butyl methacrylate, 2-ethylhexyl methacrylate, methyl methacrylate, salts of any acids and amines listed above, and mixtures thereof.

POLYSILOXANE MACROMONOMER UNITS

The copolymers of the present invention comprise from about 2% to about 50%, preferably from about 5% to about 40%, and more preferably from about 10% to about 30%, by weight of the copolymer of polysiloxane macromonomer units.

The polysiloxane macromonomer units are copolymerizable with the vinyl monomers, said macromonomers preferably having a vinyl moiety. Either a single type of macromonomer unit or combinations or two or more macromonomer units can be utilized herein. The macromonomers are selected to meet the requirements of the copolymer. By "copolymerizable", as used herein, is meant that the macromonomers can be reacted with or polymerized with the vinyl monomers in a polymerization reaction using one or more conventional synthetic techniques, as described above.

The polysiloxane macromonomers that are useful herein contain a polymeric portion and a copolymerizable moiety which is preferably an ethylenically unsaturated moiety. Typically, the preferred macromonomers are those that are endcapped with the vinyl moiety. By "endcapped" as used herein is meant that the vinyl moiety is at or near a terminal position of the macromonomer.

The macromonomers can be synthesized utilizing a variety of standard synthetic procedures familiar to the polymer chemist of ordinary skill in the art. Furthermore, these macromonomers can be synthesized starting from commercially available polymers. Typically, the weight average molecular weight of the macromonomer is from about 1000 to about 50,000.

Polysiloxane macromonomers are exemplified by the general formula:

wherein X is a vinyl group copolymerizable with the vinyl monomer units; Y is a divalent linking group; each R is independently selected from the group consisting of hydrogen, hydroxyl, C1–C6 alkyl, C1–C6 alkoxy, C2–C6 alkylamino, styryl, phenyl, C1–C6 alkyl or alkoxy-substituted phenyl; Z is a monovalent siloxane polymeric moiety having a number average molecular weight of at least about 1000, is essentially unreactive under copolymerization conditions, and is pendant from the vinyl polymeric backbone described above; n is 0 or 1; and m is an integer from 1 to 3. The polysiloxane macromonomer has a weight average molecular weight from about 1000 to about 50,000, preferably from about 5,000 to about 30,000, more preferably from about 8,000 to about 25,000.

Preferably, the polysiloxane macromonomer has a formula selected from the following formulas:

or or

In these structures s is an integer from 0 to 6; preferably 0, 1, or 2; more preferably 0 or 1; m is an integer from 1 to 3, preferably 1; p is 0 or 1; q is an integer from 2 to 6; each $R^1$ is independently selected form the group consisting of hydrogen, hydroxyl, C1–C6 alkyl, C1–C6 alkoxy, C2–C6 alkylamino, phenyl, C1–C6 alkyl or alkoxy-substituted phenyl, preferably C1–C6 alkyl, or C1–C6 alkyl or alkoxy-substituted phenyl, more preferably C1–C6 alkyl, even more preferably methyl, $R^2$ is selected from the group consisting of C1–C6 alkyl or C1–C6 alkyl substituted phenyl, preferably methyl.

n is an integer from 0 to 4, preferably 0 or 1, more preferably 0; X is wherein $R^3$ is hydrogen or —COOH, preferably $R^3$ is hydrogen; $R^4$ is hydrogen, methyl or —CH$_2$COOH, preferably $R^4$ is methyl; Z is wherein $R^5$, $R^6$, and $R^7$, are independently selected from hydrogen, hydroxyl, C1–C6 alkyl, C1–C6 alkoxy, C2–C6 alkylamino, styryl, phenyl, C1–C6 alkyl or alkoxy-substituted phenyl, hydrogen or hydroxyl, preferably $R^5$, $R^6$, and $R^7$ are C1–C6 alkyls; more preferably methyl; and r is an integer of from about 14 to about 700, preferably about 60 to about 400, and more preferably about 100 to about 170.

SILICONE BLOCK COPOLYMERS

Also useful herein are silicone block copolymers comprising repeating block units of polysiloxanes.

Examples of silicone-containing block copolymers are found in U.S. Pat. No. 5,523,365, to Geck et al., issued Jun. 4, 1996; U.S. Pat. No. 4,689,289, to Crivello, issued Aug. 25, 1987; U.S. Pat. No. 4,584,356, to Crivello, issued Apr. 22, 1986; Macromolecular Design, Concept & Practice, Ed: M. K. Mishra, Polymer Frontiers International, Inc., Hopewell Jct., NY (1994), and Block Copolymers, A. Noshay and J. E. McGrath, Academic Press, NY (1977), which are all incorporated by reference herein in their entirety.

The silicone-containing block copolymers of the present invention can be described by the formulas A-B, A-B-A, and -(A-B)$_n$- wherein n is an integer of 2 or greater. A-B represents a diblock structure, A-B-A represents a triblock structure, and -(A-B)$_n$- represents a multiblock structure.

The silicone block portion, A, can be represented by the following polymeric structure wherein each R is independently selected from the group consisting of hydrogen, hydroxyl, C1–C6 alkyl, C1–C6 alkoxy, C2–C6 alkylamino, styryl, phenyl, C1–C6 alkyl or alkoxy-substituted phenyl, preferably wherein R is methyl. In the preceding formula, m is an integer of about 10 or greater, m is an integer of about 40 or greater, more preferably of about 60 or greater, and most preferably of about 100 or greater.

The nonsilicone block, B, comprises monomers selected from the vinyl monomers as described above for the silicone grafted copolymers.

The block copolymers can comprise mixtures of diblocks, triblocks, and higher multiblock combinations as well as small amounts of homopolymers.

SULFUR-LINKED SILICONE CONTAINING COPOLYMERS AND SULFUR-LINKED SILICONE BLOCK COPOLYMERS

Also useful herein are sulfur-linked silicone containing and block copolymers. As described above, the term "sulfur-linked" means that these containing and block copolymers contain a sulfur linkage (i.e. —S—), a disulfide linkage (i.e. —S—S—), or a sulfhydryl group (i.e. —SH).

These sulfur-linked silicone containing and block copolymers are represented by the following general formula:

wherein $G_5$ represents monovalent moieties which can independently be the same or different selected from the group consisting of alkyl, aryl, alkaryl, alkoxy, alkylamino, fluoroalkyl, hydrogen, and -ZSA; A represents a vinyl polymeric segment consisting essentially of polymerized free radically polymerizable monomer, and Z is a divalent linking group. Useful divalent linking groups Z include but are not limited to the following: $C_1$ to $C_{10}$ alkylene, alkarylene, arylene, and alkoxyalkylene. Preferably, Z is selected from the group consisting of methylene and propylene for reasons of commercial availability.

$G_6$ represents monovalent moieties which can independently by the same or different selected from the group consisting of alkyl, aryl, alkaryl, alkoxy, alkylamino, fluoroalkyl, hydrogen, and -ZSA;

G₂ comprises A;
G₄ comprises A;
R₁ represents monovalent moieties which can independently be the same or different and are selected from the group consisting of alkyl, aryl, alkaryl, alkoxy, alkylamino, fluoroalkyl, hydrogen, and hydroxyl. Preferably, R₁ represents monovalent moieties which can independently be the same or different selected from the group consisting of $C_{1-4}$ alkyl and hydroxyl for reasons of commercial availability. Most preferably, R₁ is methyl.

R₂ can independently be the same or different and represents divalent linking groups. Suitable divalent linking groups include but are not limited to the following: $C_1$ to $C_{10}$ alkylene, arylene, alkarylene, and alkoxyalkylene. Preferably, R₂ is selected from the group consisting of $C_{1-3}$ alkylene and $C_7$-$C_{10}$ alkarylene due to ease of synthesis of the compound. Most preferably, R₂ is selected from the group consisting of —CH₂—, 1,3-propylene, and R₃ represents monovalent moieties which can independently be the same or different and are selected from the group consisting of alkyl, aryl, alkaryl, alkoxy, alkylamino, fluoroalkyl, hydrogen, and hydroxyl. Preferably, R₃ represents monovalent moieties which can independently be the same or different selected from the group consisting of $C_{1-4}$ alkyl and hydroxyl for reasons of commercial availability. Most preferably, R₃ is methyl.

R₄ can independently be the same or different and represents divalent linking groups. Suitable divalent linking groups include but are not limited to the following: $C_1$ to $C_{10}$ alkylene, arylene, alkarylene, and alkoxyalkylene. Preferably, R₄ is selected from the group consisting of $C_{1-3}$ alkylene and $C_7$-$C_{10}$ alkarylene for ease of synthesis. Most preferably, R₄ is selected from the group consisting of —CH₂—, 1,3-propylene, and x is an integer of 0–3;
y is an integer of 5 or greater; preferably y is an integer ranging from about 14 to about 700, preferably from about 100 to about 170;
q is an integer of 0–3;
wherein at least one of the following is true:
q is an integer of at least 1;
x is an integer of at least 1;
G₅ comprises at least one -ZSA moiety;
G₆ comprises at least one -ZSA moiety.

As noted above, A is a vinyl polymeric segment formed from polymerized free radically polymerizable monomers. The selection of A is typically based upon the intended uses of the composition, and the properties the copolymer must possess in order to accomplish its intended purpose. If A comprises a block in the case of block copolymers, a polymer having AB and ABA architecture will be obtained depending upon whether a mercapto functional group —SH is attached to one or both terminal silicon atoms of the mercapto functional silicone compounds, respectively. The weight ratio of vinyl polymer block or segment, to silicone segment of the copolymer can vary. The preferred copolymers are those wherein the weight ratio of vinyl polymer segment to silicone segment ranges from about 98:2 to 50:50, in order that the copolymer possesses properties inherent to each of the different polymeric segments while retaining the overall polymer's solubility.

Sulfur linked silicone copolymers are described in more detail in U.S. Pat. No. 5,468,477, to Kumar et al., issued Nov. 21, 1995, and PCT Application No. WO 95/03776, assigned to 3M, published Feb. 9, 1995, which are incorporated by reference herein in their entirety.

NEUTRALIZED COPOLYMERS

As is known in the art, polymers which have acidic functionalities, such as carboxyl groups, are usually used in at least partially neutralized form to promote solubility/dispersibility of the polymer. In addition, use of the neutralized form aids in the ability of the dried hair spray compositions to be removed from the hair by shampooing. When neutralized, it is preferred that from about 10% to 100%, more preferably from about 20% to about 90%, and even more preferably from about 40% to about 85%, of the acidic monomers of the copolymer be neutralized.

Any conventionally used base, including organic or inorganic (metallic or other) bases, can be used for neutralization of the polymers. Metallic bases are particularly useful in the present compositions. Hydroxides, where the cation is ammonium, an alkali metal or an alkaline earth metal, are suitable neutralizers for use in the present hair spray compositions. Preferred neutralizing agents for use in hair spray compositions of the present invention are potassium hydroxide and sodium hydroxide. Examples of other suitable neutralizing agents which may be included in the hair spray compositions of the present invention include amines, especially amino alcohols such as 2-amino-2-methyl-1,3-propanediol (AMPD), 2-amino-2-ethyl-1,3-propanediol (AEPD), 2-mino-2-methyl-1-propanol (AMP), 2-amino-1-butanol (AB), monoethanolamine (MEA), diethanolamine (DEA), triethanolamine (TEA), monoisopropanolamine (MIPA), diisopropanolamine (DIPA), triisopropanolamine (TIPA) and dimethyl stearamine (DMS). Particularly useful neutralizing agents are mixtures of amines and metallic bases.

Polymers having basic functionalities, e.g., amino groups, are preferably at least partially neutralized with an acid, e.g., hydrochloric acid.

Neutralization can be accomplished by techniques well known in the art, and before or after polymerization of the monomers comprising the graft copolymer.

Solubility of the copolymer, as described above, should be determined after neutralization, if any, as well as after addition of other ingredients that may be included in the copolymer/solvent systems.

PREFERRED POLYMERS OF THE PRESENT INVENTION

Nonlimiting examples of preferred polymers of the present invention include those selected from the group consisting of poly[(t-butylacrylate-co-n-butylacrylate-co-acrylic acid)-graft-poly(dimethylsiloxane)], poly[(t-butylacrylate-co-2-methoxyethyl acrylate-co-acrylic acid)-graft-poly(dimethylsiloxane)], poly(t-butylacrylate-co-acrylic acid)-graft-[poly(isobutylene); poly (dimethylsiloxane)], poly(4-t-butylstyrene-co-methacrylic acid)-graft-[(poly(isobutylene); poly(dimethysiloxane)], poly[(t-butylstyrene-co-methacrylic acid)]-graft-[poly(2- ethylhexyl methacrylate), poly(dimethylsiloxane)], poly[(t-butylacrylate-co-2-methoxyethyl acrylate-co-methacrylic acid)]-graft[poly(n-propyl methacrylate-co-methacrylic acid); poly(dimethylsiloxane)], poly[(t-butylacrylate-co-2-methoxyethyl acrylate-co-methacrylic acid)]-graft-poly(n-propyl methacrylate-co-acrylic acid); poly (dimethylsiloxane)], poly[(t-butylacrylate-co-2-methoxyethyl acrylate-co-methacrylic acid)]-graft-[poly(styrene-co-methacrylic acid); poly(dimethylsiloxane)], [poly(dimethyl siloxane)-block-poly(t-butylacrylate-co-n-butylacrylate-co-acrylic acid-co-methacrylic acid)]$_n$, [poly(dimethyl siloxane)-block-poly(t-butylacrylate-co-n-butylacrylate-co-acrylic acid-co-methacrylic acid)-block-poly(dimethyl siloxane)], poly(dimethyl siloxane)-block-poly(t-butylacrylate-co-n-butylacrylate-co-acrylic acid-co-methacrylic acid) and mixtures thereof.

Nonlimiting examples of preferred polymers of the present invention include those selected from the group consisting of poly[(t-butylacrylate-co-2-methoxyethyl acrylate-co-methacrylic acid)]-graft-[poly(n-propyl methacrylate-co-methacrylic acid); poly (dimethylsiloxane)], poly[(t-butylacrylate-co-n-butylacrylate-co-acrylic acid)-graft-poly (dimethylsiloxane)], [poly(dimethyl siloxane)-block-poly(t-butylacrylate-co-n-butylacrylate-co-acrylic acid-co-methacrylic acid)]$_n$,[poly(dimethyl siloxane)-block-poly(t-butylacrylate-co-n-butylacrylate-co-acrylic acid-co-methacrylic acid)-block-poly(dimethyl siloxane)].

More specific examples of copolymers of the present invention include the following, where the composition is given as weight percentage of each monomer used in the polymerization reaction (i.e. the weight percentage of the monomers and macromonomers charged).

poly(t-butylacrylate-co-2-methoxyethylacrylate-co-acrylic acid)-graft-[poly(n-propyl methacrylate-co-methacrylic acid);poly(dimethylsiloxane)] having a weight average molecular weight of about 150,000, comprising about 22% t-butylacrylate, 36% 2-methoxyethylacrylate, 18% acrylic acid, 6% poly(dimethylsiloxane) macromonomer with a weight average molecular weight of about 10,000, 18% poly(propylmethacrylae-co-methacrylic acid) macromonomer with a weight average molecular weight of about 6000.

[poly(dimethyl siloxane)-block-poly(t-butylacrylate-co-n-butylacrylate-co-acrylic acid-co-methacrylic acid)]$_n$, having a weight average molecular weight of about 100,000, comprising about 62% t-butylacrylate, 11% acrylic acid, 10% methacrylic acid, 17% poly(dimethylsiloxane) macroazoinitiator with a molecular weight of about 10,000.

poly(t-butylacrylate-co-n-butylacrylate-co-methacrylic acid-co-acrylic acid)-graft-poly(dimethylsiloxane) having a weight average molecular weight of about 150,000, comprising about 43% t-butylacrylate, 27% n-butylacrylate, 10% methacrylic acid, 10% acrylic acid, and 10% poly(dimethylsiloxane) macromonomer with a molecular weight of about 10,000.

poly[(t-butylacrylate-co-2-methoxyethyl acrylate-co-acrylic acid)-graft-[poly(isobutylene);poly(dimethylsiloxane)] having a weight average molecular weight of about 200,000, comprising about 40% t-butylacrylate, 20% n-butylacrylate, 20% acrylic acid, 10% poly(dimethylsiloxane) macromonomer with a molecular weight of about 10,000, and 10% poly(isobutylene) macromonomer with a molecular weight of about 4,000.

SOLVENT

The compositions of the present invention comprise from about 70% to about 99.9%, preferably from about 75% to about 98%, and more preferably from about 85% to about 98%, by weight of the composition, of a solvent for the copolymer. The solvent is selected from the group consisting of water, ethanol, n-propanol, isopropanol, and mixtures thereof.

Where water and alcohol mixtures are used, for instance, water-ethanol or water-isopropanol-ethanol, the water content of the compositions is generally in the range of from about 0.5% to about 99%, preferably from about 5% to about 50%, by weight of the total composition. In such mixtures, the alcohol solvents are generally present in the range of from 0.5% to about 99%, preferably from about 50% to about 95%, by weight of the total composition.

In yet another aspect of this invention are provided hair spray compositions which contain reduced levels of volatile organic compounds such as solvents. As used herein, "volatile organic compounds" or "VOCs" are those organic compounds that contain less than 12 carbon atoms or have a vapor pressure greater than about 0.1 mm of mercury. A reduced volatile organic compound hair spray composition of the present invention contains no more than 80% volatile organic compounds.

PROPERTIES OF THE DRIED HAIR SPRAY COMPOSITIONS

The hair spray compositions of the present invention, when dried, have specific physical properties as defined by the cohesive strength and total energy absorption per unit area. The dried hair spray compositions also exhibit specific impact strength properties. The hair spray compositions also preferably have an improved removeability as defined in terms of hair stiffness and flaking values.

COHESIVE STRENGTH (KGF/MM$^2$)

Cohesion is the strength of the bonds formed within a sample, e.g., a dried hair spray composition. The cohesive strength, which is designated as kgf/mm$^2$ (kilograms of force per square millimeter) is the maximum unit stress a material will withstand when being subjected to displacement in tension. Stress is the ratio of measured load (kg×f) to the original cross-sectional area (mm$^2$) of the sample.

The cohesive strength of dried hair spray compositions of the current invention are determined using the following method. This method is based on ASTM Designation: D 638-91, Standard Test Method for Tensile Properties of Plastics, Published January 1992, herein incorporated by reference in its entirety. The following test method to measure cohesive strength is similar to the ASTM standard, however, several modifications are made to better represent the tensile properties of the dried hair spray films. The measurements are made at about 73°° F. and about 50% relative humidity. The test method, described herein specifically uses a modified dumbbell shape with a thickness equal to about 0.4 mm., and uses an Instron Model Mini-55 (available from Instron Corp., Canton, Mass.) as the testing machine for applying the force to the polymer film samples.

Figure 1:
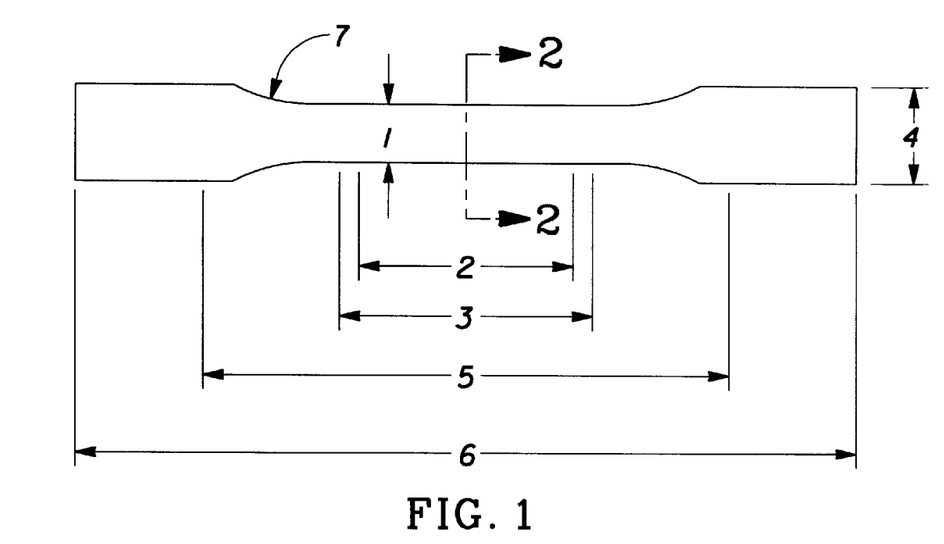
FIG. 1 illustrates an overhead view of a dumbbell-shaped planar dried hair spray film sample useful for measuring the physical properties such as the cohesive strength and total energy absorption per unit volume as described herein.
Figure 2:
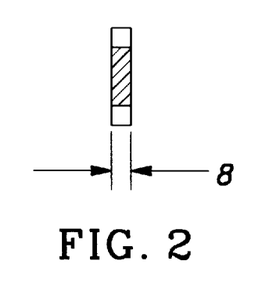
FIG. 2 illustrates a cross-sectional view, showing the thickness of the dumbbell-shaped dried film illustrated in FIG. 1.

A dried film sample is prepared by drying an amount of the hair spray composition (i.e., the silicone-containing adhesive copolymer and solvent selected from the group consisting of water, ethanol, n-propanol, isopropanol, and mixtures thereof, and any additional optional components) in a flat-bottomed aluminum mold coated with PFA (perfluoroalkoxy) Teflon®. The copolymer film is dried at about 73° F. and about 50% relative humidity until film has attained a "constant weight". By "constant weight" is meant that there is less than a 1% weight fluctuation in the sample over a period of 24 hours. The drying film should be kept in an area protected from air currents, which could result in non-uniform drying and formation of air bubbles. The copolymer film is cut into a dumbbell shape for testing. The sample should be substantially free of defects, i.e. cracks, chips, tears, etc. FIGS. 1 and 2 illustrate the planar dumbbell shaped film to be used in the tensile testing described herein for the cohesive strength and the total energy absorption per unit volume. FIG. 1 illustrates an overhead view of the dumbbell shaped sample. FIG. 2 illustrates a cross section through the dumbbell shaped sample. The width of the narrow section, 1, of the dumbbell is about 3 mm (1=3 mm). The length of the narrow, 3 mm., section of the dumbbell, 3, is about 13 mm. (3=13 mm.). The gauge length of the narrow section, 2, is the initial film length used in the determination of the strain of the sample. The gauge length is equal to or less than the length of the narrow section, preferably equal to the length of the narrow section (i.e., 2=3). The width of the ends of the dumbbell, 4, are about 10 mm. (4=10 mm.). The distance between end sections of the film, 5, is about 28 mm. (5=28 mm.). The overall length of the film, 6, is about 64 mm. (6=64 mm.). The length of the wide ends of the film is about 18 mm. ((6–5)/2=18 mm.). The transition sections between the wide ends and the narrow section of the film are about 6.5 mm. in length (i.e. (5–3)/2=6.5 mm.). Also the end portions of the narrow, center portion should be smoothly curved to avoid any stress points in the sample. The curve of the transition section, should have a radius, 7, of from about 0.5 in. to about 5 inches, and should join tangentially to the narrow section. The film is formed to a thickness, 8, of 0.4 mm. (8=0.4 mm.). The dumbbell shaped samples are further equilibrated to a "constant weight". By "constant weight" is meant that over a selected 4 day period, there is no more than 0.2% average weight gain or loss, relative to the dumbbell's measured weight 4 days previous and no more than ±0.2% weight drift should be observed between two consecutive measurements in the four day period of time. The dumbbell should be tested within a 7 day period of reaching this constant weight.

The samples are tested on a calibrated Instron Model Mini-55 tensile tester. Before mounting the sample into the Instron, the length, 3, width, 1, and thickness, 8, of the narrow section of the dumbbell shaped sample are measured to the nearest micron with a calibrated micrometer. The dimensional measurements are required by the Instron for force per unit area calculations. The wide ends of the dumbbell samples are clamped into the Instron and pulled at a crosshead rate of 5 mm. per minute. The Instron tester measures the overall forces (e.g., kgf) applied to the film. These forces are spread over the cross sectional area of the narrow section of the film. The cohesive strength of the copolymer is the maximum unit force measured by the Instron divided by the cross sectional area of the narrow portion of the film.

The dried hair spray compositions of the present invention have a cohesive strength of greater than about 0.5 kgf/mm$^2$, preferably greater than about 0.6 kgf/mm$^2$, and more preferably greater than about 0.7 kgf/mm$^2$.

TOTAL ENERGY ABSORPTION PER UNIT VOLUME (E.G., KGFMM/MM$^3$)

The total energy absorption per unit volume, which is designated as kgfmm/mm$^3$ (kilograms of force millimeters per millimeter cubed), is the ratio of the total energy required to reach the autobreak point (in kgf×mm) to the original volume of the sample (mm$^3$). The total energy required to reach the break point is calculated using standard techniques by determining the area under a load versus displacement curve for the sample. The total energy absorption per unit volume is also known as "toughness" by those skilled in the art of polymer science and materials testing.

The measurements are made at about 73° F. and about 50% relative humidity.

The dried hair spray compositions of the present invention have a total energy absorption per unit volume of greater than about 0.55 kgfmm/mm$^3$, preferably greater than about 0.75 kgfmm/mm$^3$, more preferably greater than about 1.10 kgfmm/mm$^3$, more preferably greater than about 1.60 kgfmm/mm$^3$, and most preferably greater than about 2.15 kgfmm/mm$^3$.

IMPACT STRENGTH

Impact strength is the mean-failure energy (mass×gravity×height) required to produce sample failure, e.g., in a dried hair spray composition. The sample failure is characterized by a crack or split created by the impact of the falling weight that can be seen by the naked eye under normal laboratory lighting conditions.

The impact strength of the dried hair spray compositions of the current invention are determined using the following method. This method is based on ASTM Designation: D 5420-93, Standard Test Method for Impact Resistance of Flat, Rigid Plastic Specimen by Means of a Striker Impacted by a Falling Weight (Gardner Impact), Published 1995, herein incorporated by reference in its entirety, however, several modifications are made to better represent the impact properties of the dried film. The measurements are made at about 73° F. and about 50% relative humidity.

The test method, described herein specifically uses rectangular shaped samples with a thickness equal to about 0.4 mm, and uses a GCA/Precision Scientific Penetrometer modified to drop a blunt faced probe to a distance of 70 mm and equipped with a Precision Scientific solenoid controller for GCA Penetrometer, a blunt faced cylindrical probe with a surface area of 8 mm$^2$ (OK M&T Corp.-part # WSU30), and a ruler which measures in 1 mm increments.

The samples are prepared using the film drying method described above in the cohesive strength measurements. The copolymer film is cut into the rectangular shape, e.g. 10 mm×20 mm. The thickness of the sample is 0.4 mm. The film thickness of various test samples should be maintained within ±15% of 0.4 mm.

The following measurement process is used. Turn on the solenoid operated probe release controller. The controller should begin to cycle on and off as indicated by a red light. Be sure the probe face is flush with the impact surface so that the sharp edge of the probe does not strike the film. Place a film sample on the Impact Tester over the target area. Direct the metric ruler gently on the film sample. Direct the lightening source across the surface of the sample such that the light source is in the same plane as the surface of the film. Small fractures in the film will reflect light and be easily detected. Move the probe up to desired drop distance. A suggested distance progression is: 1 mm, 3 mm, 5 mm, 10 mm, 15 mm, 20 mm, 25 mm, and further 5 mm increments up to 70 mm. (70 mm is the upper limit of the instrument). Turn on the instrument switch, to drop the probe onto the sample. The first step in the measurement of impact energy is to find the range of probe height necessary to fracture the film. Start at 1 mm for the first step. Continue to move up according to the suggested distance progression until a fracture is observed. When a fracture is observed make a note of it and move to a new sample. The second step in determining impact energy is to set a new sample and start drop at an observed fracture point in the range procedure. Set a new film sample and move the probe to the next lowest setting. If the film fractures, record result and repeat previous step. If the film does not fracture, set a new sample and move to the next distance. Continue to set new samples and increase the drop distance until the film fractures. Continue the procedure until 5 fractures are observed. Calculate the amount of work energy, i.e. the fracture strength using the following formula:

W=m×g×h, where

W=amount of work energy in ergs, m=mass of probe (59.53 g) (The probe is removable and can be replaced with one of different mass or impact surface area).

g=gravitational constant (980.665 cm/sec$^2$), h=average distance probe travels to impact (cm).

The dried hair spray compositions of the present invention have an impact strength of greater than about 7000 ergs, preferably greater than about 20,000 ergs, and more preferably greater than about 50,000 ergs.

HAIR SPRAY REMOVEABILITY

The adhesive copolymers herein have improved removeability when used in the preferred hairspray embodiments of the present invention. In this context, removeability means that the adhesive copolymers are more easily removed from the hair or other applied surface during shampooing.

For purposes of defining the preferred hair spray compositions of the present invention, removeability is determined indirectly by evaluating hair stiffness and the appearance of observable white flakes after treating the hair in accordance with the removeability methodology described hereinafter. It has been found that the removeability of a hair spray formulation after shampooing correlates with the resulting stiffness/softness of the hair and the appearance/nonappearance of white flakes on the hair after a series of shampooing cycles. The hair spray compositions of the present invention have high removeability e.g., reduced stiffness and reduced white flaking. The term "removeability" as used herein therefore refers to hair stiffness values (0–4 scale) and white flaking values (0–4 scale) as measured in accordance with the methodology described hereinafter.

For purposes of the defining the preferred hair spray compositions of the present invention, the removeability of the hair spray compositions is defined as a combination of hair stiffness values and hair flaking values, wherein the hair spray compositions provide hair flaking values ranging from 0 to about 3.5, preferably from 0 to about 2.5, more preferably from 0 to about 2.0, and hair stiffness values ranging from 0 to about 3.5, preferably from 0 to about 2.5, more preferably from 0 to about 2.0.

METHODOLOGY: HAIRSPRAY REMOVEABILITY

Removeability of the hairspray composition of the present invention, as indirectly evaluated in terms of hair stiffness and the appearance of white flakes, is determined in accordance with the following methodology. The methodology simulates multiple application and multi-cycle application of hairspray compositions so as to indirectly determine how readily and effectively such hairspray compositions are removed from hair.

The methodology described herein provides a means of evaluating hair switches blindly treated with hairspray embodiments of the present invention. The method by which each hair switch is treated with the hairspray embodiments, and the method by which each treated hair switch is then evaluated for removeability are described in detail below.

Two trained panelists each evaluate identically treated hair switches or sets of hair switches for stiffness and the appearance of white flakes. The panelists then individually assign each of the treated hair switches with a numerical score (0 to 4 scale) for hair stiffness and a numerical score for flaking (0 to 4 scale). The order in which the hair switches are treated with different hair spray embodiments is randomized and conducted round robin. Two identical sets of switches are prepared as described below for each panelist so that each has a fresh set of switches to evaluate. Before evaluating the blindly treated hair switches, each panelist also evaluates (not blinded) an untreated hair switch as a zero reference for hair stiffness and flaking. Each panelist also evaluates a control treated hair switch as a flaking reference (score 4.0) and another control treated hair switch as a hair stiffness reference (score 4.0). The hair stiffness values as defined herein are determined by averaging the hair stiffness scores provided by the two panelist. Likewise, the hair flaking values as defined herein are determined by averaging the hair flaking scores provided by the two panelists.

The hair switches are treated with either an aerosol or non-aerosol hair spray embodiment of the present invention in accordance with the following steps. The hair stiffness reference and the flaking reference are also prepared in accordance with the following steps, except that each is treated with the corresponding hair spray formulations as described hereinafter in Tables 2 and 3.

1) Vertically suspend a clean hair switch (10 inch European virgin brown hair, 20 gram) from its bound end and comb (black rubber comb, 5 inches by 1 inch, ½ fine tooth) through the switch to remove any tangles.

2) If necessary, use a static gun to eliminate any static build-up on the switch.

3) For non-aerosol products, spray the switch from a distance of 4 inches while applying ten pumps of the product to the switch and while moving the atomized spray pattern in a fluid up-and-down motion to cover the entire switch, or for aerosol products, spray each switch from a distance of 6 inches while applying the aerosol stream to the switch for a period of 3 seconds and while moving the aerosol stream in a fluid up-and-down motion to cover the entire switch.

4) Repeat step 3 on the opposite side of the switch.

5) After spraying the opposite side of the switch, hang the treated switch from its bound end to allow it to dry for one hour at ambient temperature, pressure and humidity.

6) Comb the dried switch using a black rubber comb (5 inches×1 inch, ½ inch fine tooth) by combing away from the bound end of the switch but by initially starting toward the unbound end taking smaller strokes and then gradually taking larger strokes until the comb passes through the entire unbound length of the treated switch.

7) Repeat steps 1 through 6.

8) Wet the treated hair switch with water (+15–20 grain hardness, 38° C., 1 gal/min. water pressure).

9) Apply 1 ml of shampoo (Table 1: methodology shampoo) along the length of the front of the wet hair switch and apply another 1 ml of the shampoo along the length of the reverse side of the wet hair switch.

10) Gently milk the switch from top to bottom (hand over hand between thumb and fingers) for 15 seconds at 1 stroke per second.

11) Rinse the hair switch with water (38° C., +15–20 grain hardness, 1 gal/min. water pressure) for 15 seconds. Gently squeeze the hair between the first and second fingers, drawing the fingers down the switch after 5 seconds, 10 seconds, and after final rinse.

12) Hang the treated switch and allow it to dry for two hours at 60° C. in a hot box.

13) Remove the dried switches from the hot box.

14) Comb the dried switch using a black rubber comb (5 inches×1 inch, ½ inch fine tooth) by combing away from the bound end of the switch but by initially starting toward the unbound end taking smaller strokes and then gradually taking larger strokes until the comb passes through the entire unbound length of the treated switch.

15) Repeat steps 1–14.

16) Repeat steps 1–13.

17) A panelist then evaluates the treated switch by feeling it between their first and second fingers of their dominant hand and between their thumb and other fingers for stiffness and resistance to bending, and then assigns to the treated switch a hair stiffness score (0 to 4 scale). The value of the assigned score is relative to the hair stiffness reference score (4) and the untreated reference score (0).

18) The panelist then combs the evaluated switch in accordance with the procedure set forth in Step 14 above, and then visually evaluates the combed switch for white flakes, coating, and white haze and assigns it a hair flaking score (0 to 4 scale). The value of the assigned score is relative to the hair flaking reference score (4) and the untreated reference score (0).

TABLE 1

Methodology Shampoo

| Ingredient List | Percent Composition As Added | Percent Composition Chemical Content |
|---|---|---|
| Sodium Laureth Sulfate | 40.0000 | 10.0000 |
| Water - USP Purified | 30.3000 | 30.3000 |
| Sodium Lauryl Sulfate | 29.1000 | 8.0025 |
| Cocamide DEA | .5000 | .4000 |
| Kathon CG | .1000 | .0015 |
| Citric Acid Solution (50% active) | ** adj. from 0–1% (note: water level qs. to 100%) | |

TABLE 2

High Flaking Control

| Raw Materials | Percent Composition As Added | Percent Composition Chemical Content |
|---|---|---|
| Octylacrylamide/Acrylates/Butylaminoethyl Methacrylate Copolymer (National Starch lot AF-6713) | 4.50 | 4.50 |
| Water - USP Purified | 15.50 | 15.50 |
| Ethanol (SDA 40) | 80.00 | 80.00 |

TABLE 3

High Stiffness Control

| Raw Materials | Percent Composition As Added | Percent Composition Chemical Content |
|---|---|---|
| Octylacrylamide/Acrylates/Butylaminoethyl Methacrylate Copolymer (National Starch lot AF-6713) | 6.00 | 6.00 |
| Aminomethylpropanol, 95% | 1.04 | 0.99 |
| Water - USP Purified | 15.50 | 15.50 |
| Diisobutyl Adipate | 0.20 | 0.20 |
| Ethanol (SDA 40) | 80.00 | 80.00 |

Each of the formulations described in Tables 1–3 are prepared by conventional formulation and mixing techniques.

OPTIONAL INGREDIENTS

The compositions of the present invention can also comprise a wide variety of optional ingredients that are suitable for application to human hair.

The compositions hereof can optionally contain a plasticizer for the copolymer. Any plasticizer suitable for use in hair care products or for topical application to the hair or skin can be used. A wide variety of plasticizers are known in the art. These include glycerin, diisobutyl adipate, butyl stearate, propylene glycol, tri-$C_2$-$C_8$ alkyl citrates, including triethyl citrate and tri-propyl, -butyl, -pentyl, etc., analogs of triethyl citrate. Triethyl citrate is preferred.

Plasticizers are typically used at levels of from about 0.01% to about 10%, by weight of the composition, preferably from about 0.05% to about 3%, more preferably from about 0.05% to about 1%. Preferably, the weight ratio of graft copolymer to the plasticizer is from about 1:1 to about 40:1, preferably from about2:1 to about 30:1, more preferably from about 3:1 to about25:1.

Optionally, the compositions of the present invention can contain an effective amount of a non-surface active ionic strength modifier system for reducing the viscosity of the hair spray composition. When used, the ionic strength modifiers will be present in the present compositions at a level of at least about 0.01%, by weight of the composition. The upper limit is dependent upon the maximum amount of the ionic strength modifiers that can be present in the particular compositions hereof such that the hair setting resin remains solubilized or dispersed. As will be understood by those skilled in the art, as the ionic strength of the composition is increased, the resin will eventually fall out of solution, or otherwise no longer remain solubilized or dispersed in the hydrophilic liquid carrier. The upper limit of the ionic strength modifier system level will vary depending upon the particular ionic strength modifiers, liquid vehicle, resin, and other ingredients present in the composition. Thus, for example, the maximum amount of the ionic strength modifiers that can be used will tend to be lower for compositions with liquid vehicles containing less water, compared to compositions with more water. Generally, the compositions will comprise about 4%, by weight, or less of the ionic strength modifiers, more generally about 2% or less, and typically about 1% or less. Preferably, the compositions hereof will comprise from about 0.01% to about 0.5%, more preferably from about 0.01% to about 0.1%, of the ionic strength modifier system.

The ionic strength modifier system comprises a mixture of monomeric cations and anions. The ions of the ionic strength modifier system hereof are non-surface active, i.e. they do not significantly reduce surface tension. For purposes hereof, non-surface active shall mean the ions, which at a 0.5% aqueous solution concentration, reduce surface tension by no more than 5.0 dynes/cm$^2$. Generally, the ions of the ionic strength modifier system hereof will be characterized by having, at maximum, four or less carbon atoms per charge, preferably two or less carbon atoms, in any aliphatic chain or straight or branched chain organic heterochain.

The ionic strength modifier system comprises monomeric ions of the type which are products of acid-base reactions. Thus, basic and acidic ions OH$^-$ and H$^+$ do not constitute part of the ionic strength modifier system hereof, although they may be present in the composition. The ions hereof are incorporated into the composition in a form such that they can exist in the composition as free ions, i.e., in dissociated form. It is not necessary that all of the ions added exist in the composition as free ions, but must be at least partially soluble or dissociated in the composition. The ionic strength modifiers can be incorporated into the hair styling compositions, for example, by addition of soluble salts, or by addition of mixtures of acids and bases, or by a combination thereof. It is a necessary aspect of the invention that both anions and cations of the ionic strength modifier system be included in the composition.

Suitable cations for use include, for example, alkali metals, such as lithium, sodium, and potassium, and alkaline-earth metals, such as magnesium, calcium, and strontium. Preferred of the divalent cations is magnesium. Preferred monovalent metal ions are lithium, sodium, and potassium, particularly sodium and potassium. Suitable means of addition to the compositions hereof include, for example, addition as bases, e.g., hydroxides, sodium hydroxide and potassium hydroxide, and such as salts that are soluble in the liquid carrier, e.g. salts of monomeric anions such as those described below.

Other suitable cations include organic ions, such as quaternary ammonium ions and cationic amines, such as ammonium mono-, di-, and triethanolamines, triethylamine, morpholine, aminomethylpropanol (AMP), aminoethylpropanediol, etc. Ammonium and the amines are preferably provided in the forms of salts, such as hydrochloride salts.

Monomeric anions that can be used include halogen ions, such as chloride, fluoride, bromide, and iodide, particularly chloride, sulfate, ethyl sulfate, methyl sulfate, cyclohexyl sulfamate, thiosulfate, toluene sulfonate, xylene sulfonate, citrate, nitrate, bicarbonate, adipate, succinate, saccharinate, benzoate, lactate, borate, isethionate, tartrate, and other monomeric anions that can exist in dissociated form in the hair styling composition. The anions can be added to the compositions hereof, for example, in the form of acids or salts which are at least partially soluble in the liquid vehicle, e.g., sodium or potassium salts of acetate, citrate, nitrate, chloride, sulfate, etc. Preferably, such salts are entirely soluble in the vehicle.

The use of ionic strength modifiers are especially useful in reduced volatile organic solvent compositions.

The present compositions can also contain various hydrophobic volatile solvents such as cyclomethicone and volatile hydrocarbons such as isododecane and isohexadecane.

The present compositions can contain a wide variety of other optional ingredients, including among them any of the types of ingredients known in the art for use in hair care compositions, especially hair setting compositions such as especially hair spray compositions and hair setting tonics.

Generally, such other adjuvants collectively can comprise from about 0.05% to about 5% by weight and preferably from about 0.1% to about 3%, by weight. Such conventional optional adjuvants are well known to those skilled in the art and include, but are not limited to, surfactants (which may be anionic, cationic, amphoteric, or zwitterionic and which include fluorinated surfactants and silicone copolyols), propellants, hair conditioning agents (e.g., silicone fluids, fatty esters, fatty alcohols, long chain hydrocarbons, cationic surfactants, etc.); emollients; lubricants and penetrants such as various lanolin compounds; protein hydrolysates and other protein derivatives; ethylene adducts and polyoxyethylene cholesterol; dyes, tints, bleaches, reducing agents and other colorants; pH adjusting agents; sunscreens; preservatives; thickening agents (e.g. polymeric thickeners, such as xanthan gum); and perfume.

HAIR SPRAY PRODUCTS

The hair spray compositions of the present invention can be dispensed as sprayed or atomized products from containers which are pump spray dispensers or aerosol canisters. Such containers are well known to those skilled in the art and are commercially available from a variety of manufacturers, including American National Can Corp. and Continental Can Corp.

When the hair spray compositions are to be dispensed from a pressurized aerosol container, a propellant which consists of one or more of the conventionally-known aerosol propellants can be used to propel the compositions. A suitable propellant for use can be generally any liquifiable gas conventionally used for aerosol containers. Suitable propellants for use are volatile hydrocarbon propellants which can include liquified lower hydrocarbons of 3 to 4 carbon atoms such as propane, butane and isobutane. Other suitable propellants are hydrofluorocarbons such as 1,2-difluoroethane (Hydrofluorocarbon 152A) supplied as Dymel 152A by DuPont. Other examples of propellants are dimethylether, nitrogen, carbon dioxide, nitrous oxide, and atmospheric gas. The hydrocarbons, particularly isobutane, used singly or admixed with other hydrocarbons are preferred.

The aerosol propellant may be mixed with the present hair spray compositions and the amount of propellant to be mixed is governed by normal factors well known in the aerosol art. Generally, for liquefiable propellants, the level of propellant is from about 10% to about 60% by weight of the total composition, preferably from about 15% to about 50% by weight of the total composition.

Alternatively, pressurized aerosol dispensers can be used where the propellant is separated from contact with the hair spray composition such as a two compartment can of the type sold under the tradename SEPRO from American National Can Corp.

Other suitable aerosol dispensers are those characterized by the propellant being compressed air which can be filled into the dispenser by means of a pump or equivalent device prior to use. Such dispensers are described in U.S. Pat. Nos. 4,077,441, Mar. 7, 1978, Olofsson and 4,850,577, Jul. 25, 1989, TerStege, both incorporated by reference herein, and in U.S. Pat. No. 5,323,935 issued Jun. 28, 1994 Gosselin, et al., filed Feb. 21, 1992, also incorporated by reference herein. Compressed air aerosol containers suitable for use are also currently marketed by The Procter & Gamble Company under their tradename VIDAL SASSOON AIRSPRAY® hair sprays.

Conventional nonaerosol pump spray dispensers, i.e., atomizers, can also be used.

Other hair styling compositions include tonics and lotions, which are typically dispensed in a conventional bottle or tube, and applied directly to the hair or first dispensed to the hand and then to the hair.

METHOD OF MAKING

The hair styling compositions of the present invention can be made using conventional formulation and mixing techniques. The silicone-containing adhesive copolymer and the solvent are mixed to provide a homogeneous mixture. Any other ingredients are then added and mixed to yield the final composition. If the polymer is neutralized, the neutralizer is preferably added prior to addition of other ingredients. For hair spray products, the composition is packaged in conventional mechanical pump spray devices, or alternatively, in the case of aerosol sprays products, the composition is packaged in conventional aerosol canisters along with an appropriate propellant system.

METHOD OF USE

The compositions of the present invention are used in conventional ways to provide the hair care benefits of the present invention. Such methods generally involve application of an effective amount of the product to dry, slightly damp, or wet hair before and/or after the hair is dried and arranged to a desired style. Application of the product is normally effected by spraying or atomizing the product using an appropriate device, e.g. a mechanical pump spray, a pressurized aerosol container, or other appropriate means. The composition is then dried or allowed to dry. By "effective amount" is meant an amount sufficient to provide the hair hold and style benefits desired. In general, from about 0.5 g to about 30 g of product is applied to the hair, depending upon the particular product formulation, dispenser type, length of hair, and type of hair style.

The following Experiments and Examples further illustrate embodiments within the scope of the present invention. They are given solely for the purposes of illustration and are not to be construed as limitations of the present invention as many variations of the invention are possible without departing from its spirit and scope.

EXAMPLES

The following examples fuirther describe and demonstrate embodiments within the scope of the present invention. The examples are given solely for the purpose of illustration and are not to be construed as limitations of the present invention, as many variations thereof are possible without departing from the spirit and scope of the invention. Ingredients are identified by chemical or CTFA name.

Examples 1–4: Syntheses of Macromonomers and Copolymers

Example 1

Synthesis of Vinylphenyl-terminated Poly(n-Propyl Methacrylate-co-Methacrylic Acid) Macromonomer Into a round-bottomed-flask fitted with magnetic stirring and under slight argon pressure (8 psi), is added tetrahydrofuran (1 L), trimethylsilylmethacrylate (100 g, 0.632 mole), and n-propylmethacrylate (100 g, 0.780 mole). The solution is cooled to −80° C. then initiated with diphenylhexyllithium (0.0275 moles) for chain propagation via anionic polymerization mechanism. After continuous stirring for 0.5 h, vinylbenzoyl chloride (8.33 mL, 0.05 mole) is charged to the solution and continued stirring for 0.5 h. The solution is then warmed to ambient temperature and $H_2O$ (10 mL) is added and stirred for 0.25 hours to deprotect the acid groups. The macromonomer, which has a weight average molecular weight of about 6000, is obtained by precipitating the resulting solution in hexanes, collecting precipitate, and drying under vacuum.

Example 2

Synthesis of Poly(t-Butylacrylate-co-2-Methoxyethylacrylate-co-Acrylic Acid)-Graft-[Poly (Propyl Methacrylate-co-Methacrylic Acid);Poly (Dimethylsiloxane)] Copolymer To a round-bottomed-flask equipped with a reflux condenser, temperature control, mechanical stirring mechanism, and under slight argon pressure (8 psi), is added acetone (0.5 L), t-butylacrylate (22.3 g), 2-methoxyethylacrylate (36 g), acrylic acid (18 g), poly (dimethylsiloxane) macromonomer (6 g) (Chisso Corp. Tokyo, Japan), and vinylphenyl-terminated (n-propylmethacrylate-co-methacrylic acid) macromonomer (18 g) (from Example 1). Solution is stirred until all components are dissolved, then heated to 60C. Azobisisobutyronitrile (0.7 g) is charged to the system. After 10 h, solution is cooled and precipitated in water to yield silicone modified graft copolymer.

Example 3

Synthesis of [Poly(Dimethyl Siloxane)-Block-Poly (t-Butylacrylate-co-n-Butylacrylate-co-Acrylic Acid-co-Methacrylic Acid)]$_n$ Place 62.4 parts of t-butyl acrylate, 20.8 parts acrylic acid, 200 parts acetone (as a solvent), and 15 parts isopropanol (as a chain transfer agent) in a roundbottom flask. Separately, dissolve 16.8 parts VPS-1001 (poly(dimethyl siloxane) initiator) macroazoinitiator (commercially available from Wako Chemical USA, INC., Richmond, Va.) into 200 parts ethyl acetate and add the solution to an addition funnel. Purge the reaction vessel with argon for approximately one hour. Following the purge, maintain a constant positive pressure on the closed reaction system with argon. Heat the reaction mixture to 58° C. Add the VPS-1001 solution to the reaction flask in a dropwise fashion over the course of one hour. Maintain heating and stirring for 20 hours. Terminate the reaction by opening the reactor to the atmosphere and cooling to room temperature.

The polymer is precipitated from the solution by adding one part of the polymer solution to 15 parts water. The resultant polymer is then placed in a vacuum oven for heated drying. Following the drying, the polymer is ground and extracted for 20 hours with hexane using a soxhlet extractor. The polymer is then vacuum dried with heat in an oven.

Example 4

Synthesis of Poly(t-Butylacrylate-co-n-Butylacrylate-co-Methacrylic Acid-co-Acrylic Acid)-Graft-Poly(Dimethylsiloxane)

Place 36 parts of t-butyl acrylate, 27 parts n-butyl acrylate, 10 parts methacrylic acid, 12 parts acrylic acid, and 15 parts polydimethylsiloxane macromonomer (available from Chisso Corp., Tokyo, Japan) in a roundbottom flask. Add sufficient acetone as the reaction solvent to produce a final monomer concentration of about 20% by volume. Purge the vessel with argon for approximately one hour. Following the purge, maintain a constant positive pressure on the closed reaction system with argon. Heat the reaction mixture to 58° C. Prepare a 10% solution of azobisisobutyronitrile (0.5% by weight relative to the amount of monomer) in acetone, and add it to the reaction mixture. Maintain heat and stirring for 20 hours. Terminate the reaction by opening the reactor to the atmosphere and cooling to room temperature.

The polymer is precipitated from the solution by adding one part solution to 15 parts water. The resultant polymer is then redissolved in acetone. This procedure is repeated six times, with the final polymer being placed in a vacuum oven for heated drying.

Example 5

Synthesis of Acryloyl Encapped Polyisobutylene Macromonomer

Prepare a solution of 100 grams (0.024 mol) hydroxyl endcapped polyisobutylene polymer (PIB-OH) having a weight average molecular weight of 4,172 g/mol by conventional living carbocationic polymerization of isobutylene (for example, as described in G. Kaszas, Poly. Bull., 20, 413 (1989). Add a two fold mole excess (4.84 g, 0.048 mol) triethylamine to the solution. Add this solution dropwise to a solution of acryloyl chloride (4.35 g, 0.048 mol) in dry methylene chloride (100 g) at 0° C. Stir for about 12 hours at room temperature, filter the mixture and evaporate the excess triethylamine and methylene chloride to obtain acryloyl endcapped polyisobutylene macromonomer.

Example 6

Synthesis of Poly[(t-Butylacrylate-co-2-Methoxyethyl Acrylate-co-Acrylic Acid)-Graft-[Poly(Isobutylene);Poly(Dimethylsiloxane)]

Place 20 parts acrylic acid, 40 parts t-butyl acrylate, 20 parts n-butylacrylate, 10 parts polyisobutylene macromonomer (4172 MW) (from Example 5) in a flask, 10 parts poly(dimethylsiloxane). Add sufficient tetrahydrofuran as the reaction solvent to produce a final monomer concentration of about 20%. Purge the vessel with an inert atmosphere, preferably nitrogen or argon. Add initiator, (2,2'-azobisisobutyronitrile) to a level appropriate for the desired molecular weight. Typically this is in the range of 0.5% to 1.0% by weight relative to the amount of monomer. Heat to 60° C. and maintain this temperature for 48 hours while agitating. Terminate the reaction by cooling to room temperature. The polymer is purified by drying off the reaction solvent in an oven. Alternatively, acetone can be used in place of tetrahydrofuran, in which case the polymer is precipitated by adding water and the precipitated polymer is collected and dried.

Examples 7–14

The following examples represent nonaerosol hair spray compositions of the present invention.

|  | Example No. | | | | | | | |
| --- | --- | --- | --- | --- | --- | --- | --- | --- |
| Component (wt %) | 7 | 8 | 9 | 10 | 11 | 12 | 13 | 14 |
| Copolymer 6 | 4.00 | 5.00 | 6.00 | 4.00 | — | — | — | — |
| Copolymer 2 | — | — | — | — | 3.00 | 3.50 | 2.50 | 4.00 |
| Isododecane[1] | 1.00 | — | — | — | — | 1.0 | 2.0 | — |
| Diisobutyl adipate | 0.40 | — | 0.90 | 0.55 | — | — | — | 0.40 |
| Sodiumhydroxide[2] | 0.96 | 1.20 | 1.44 | — | — | 1.20 | — | 1.35 |
| Potassium hydroxide[3] | — | — | — | 1.21 | 1.00 | — | 0.70 | — |
| Perfume | 0.10 | 0.10 | 0.10 | 0.10 | 0.10 | 0.15 | 0.10 | 0.15 |
| Water | QS100 | QS100 | QS100 | QS100 | QS100 | QS100 | QS100 | QS100 |
| Sodium Benzoate | — | — | — | — | 0.10 | 0.10 | — | 0.10 |
| Ethanol[4] | 76.54 | 71.95 | 81.56 | 71.25 | 79.40 | 69.26 | 78.00 | 55.00 |

[1]PERMETHYL 99A, from Presperse, Inc., South Plainfield, NJ, USA.
[2]Sodium hydroxide is 30% active.
[3]Potassium hydroxide is 45% active.
[4]SDA 40 (100% ethanol).

Examples 15–20

The following examples represent aerosol hair spray compositions of the present invention.

|  | Example No. | | | | | |
| --- | --- | --- | --- | --- | --- | --- |
| Component (wt %) | 15 | 16 | 17 | 18 | 19 | 20 |
| Copolymer 3 | 5.00 | 4.00 | 3.50 | — | — | — |
| Copolymer 4 | — | — | — | 4.00 | 3.00 | 4.00 |
| Isododecane[1] | 0.50 | — | — | — | — | 0.50 |
| Triethyl citrate[2] | — | — | 0.21 | — | — | — |
| Diisobutyl adipate | 0.70 | 0.45 | — | 0.40 | 0.25 | 0.35 |
| Propylene glycol | — | — | 0.30 | — | — | — |
| Sodium hydroxide[3] | 1.00 | — | — | — | 1.0 | — |
| Potassium hydroxide[4] | — | 0.94 | 1.20 | 1.04 | — | 1.20 |
| Perfume | 0.10 | 0.10 | 0.10 | 0.10 | 0.10 | 0.10 |
| Water | QS100 | QS100 | QS100 | QS100 | QS100 | QS100 |
| Sodium Benzoate | 0.10 | 0.10 | — | 0.10 | 0.20 | — |
| Ethanol[5] | 56.69 | 57.42 | 72.0 | 50.0 | 30.00 | 54.5 |

-continued

| Component (wt %) | Example No. | | | | | |
|---|---|---|---|---|---|---|
| | 15 | 16 | 17 | 18 | 19 | 20 |
| Propellant - Isobutane | — | — | 7.02 | 15.00 | 10.00 | — |
| Propellant - n-butane | 10.00 | — | — | — | — | — |
| Propellant - Dimethyl ether[6] | 10.00 | — | — | 15.00 | 15.00 | — |
| Propellant - Hydrofluorocarbon 152a[7] | — | 25.0 | 15.98 | — | — | 32.32 |

[1]PERMETHYL 99A, from Presperse, Inc., South Plainfield, NJ, USA.
[2]CITROFLEX-2, from Morflex, Inc., Greensboro, NC, USA.
[3]Sodium hydroxide is 30% active.
[4]Potassium hydroxide is 45% active.
[5]SDA 40 (100% ethanol).
[6]DYMEL - A, from Dupont.
[7]DYMEL-152a, from Dupont.

The compositions are prepared as described above, by first mixing the polymer with the ethanol, neutralizing the polymer with sodium or potassium hydroxide, then adding sequentially (as applicable) with mixing, isododecane, plasticizer, perfume, and water. If sodium benzoate is used, it is added after water addition. Most preferably a premix of water and sodium benzoate is made and then added after the main water addition. Propellants for aerosol compositions are charged to conventional aerosol containers after the remainder of the prepared composition has been added.

The hair spray embodiments of the present invention described in Examples 5–18 have high removeability from hair, and when evaluated by the removeability methodology described herein, provide a hair stiffness value of less than 2.0 and a hair flaking value of less than 2.0.

While particular embodiments of the subject invention have been described, it will be obvious to those skilled in the art that various changes and modifications to the subject invention can be made without departing from the spirit and scope of the invention. It is intended to cover, in the appended claims, all such modifications that are within the scope of the subject invention.

What is claimed is:

1. A hair spray composition, comprising:
   (a) a silicone-containing adhesive copolymer containing one or more alkyl or aryl siloxane moieties, having a weight average molecular weight from about 10,000 to about 5,000,000 selected from the group consisting of:
      (i) poly[(t-butylacrylate-co-n-butylacrylate-co-acrylic acid)-graft-poly(dimethylsiloxane)],
      (ii) poly[(t-butylacrylate-co-2-methoxyethyl acrylate-co-acrylic acid)-graft-poly(dimethylsiloxane)],
      (iii) poly(t-butylacrylate-co-acrylic acid)-graft-[poly(isobutylene); poly(dimethylsiloxane)],
      (iv) poly(4-t-butylstyrene-co-methacrylic acid)-graft-[(poly(isobutylene); poly(dimethysiloxane)],
      (v) poly[(t-butylstyrene-co-methacrylic acid)]-graft-[poly(2-ethylhexyl methacrylate), poly(dimethylsiloxane)],
      (vi) poly[(t-butylacrylate-co-2-methoxyethyl acrylate-co-methacrylic acid)]-graft[poly(n-propyl methacrylate-co-methacrylic acid); poly(dimethylsiloxane)],
      (vii) poly[(t-butylacrylate-co-2-methoxyethyl acrylate-co-methacrylic acid)]-graft-poly(n-propyl methacrylate-co-acrylic acid); poly(dimethylsiloxane)],
      (viii) poly[(t-butylacrylate-co-2-methoxyethyl acrylate-co-methacrylic acid)]-graft-[poly(stryene-co-methacrylic acid); poly(dimethylsiloxane)],
      (ix) [poly(dimethyl siloxane)-block-poly(t-butylacrylate-co-n-butylacrylate-co-acrylic acid-co-methacrylic acid)]$_n$, wherein n=an integer of 2 or greater,
      (x) [poly(dimethyl siloxane)-block-poly(t-butylacrylate-co-n-butylacrylate-co-acrylic acid-co-methacrylic acid)-block-poly(dimethyl siloxane)],
      (xi) poly(dimethyl siloxane)-block-poly(t-butylacrylate-co-n-butylacrylate-co-acrylic acid-co-methacrylic acid)
      (xii) poly(t-butylacrylate-co-2-methoxyethylacrylate-co-acrylic acid)-graft-[poly(n-propyl methacrylate-co-methacrylic acid);poly(dimethylsiloxane)]
      (xiii) poly(t-butylacrylate-co-n-butylacrylate-co-methacrylic acid-co-acrylic acid)-graft-poly(dimethylsiloxane)
      (xiv) poly[(t-butylacrylate-co-2-methoxyethyl acrylate-co-acrylic acid)-graft-[poly(isobutylene);poly(dimethylsiloxane)]
      (xv) and mixtures thereof; and
   (b) a solvent for said copolymer selected from the group consisting of: water, ethanol, n-propanol, isopropanol, and mixtures thereof,
   wherein said hair spray composition, when dried, has a cohesive strength of greater than about 0.5 kgf/mm$^2$ and a total energy absorption per unit volume of greater than about 0.55 kgfmm/mm$^3$.

2. A hair spray composition according to claim 1 wherein said hair spray composition, when dried, has an impact strength of greater than about 7000 ergs.

3. A composition according to claim 1 wherein said copolymer is soluble or dispersible in said solvent at a concentration of at least about 0.1 mg/mL at about 73° F.

4. A composition according to claim 3 wherein said hair spray composition, when dried has a cohesive strength of greater than about 0.6 kgf/mm$^2$, a total energy absorption of greater than about 0.75 kgfmm/mm$^3$, and an impact strength of greater than about 20,000 ergs.

5. A composition according to claim 4 wherein said hair spray composition, when dried, has a cohesive strength of greater than about 0.7 kgf/mm$^2$, a total energy absorption of greater than about 1.10 kgfmm/mm$^3$, and an impact strength of greater than about 50,000 ergs.

6. A composition according to claim 5 wherein said copolymer is a silicone grafted copolymer comprising a polymeric backbone and polysiloxane side chains grafted to said backbone.

7. A composition according to claim 6 wherein said copolymer is formed from the random copolymerization of the following relative weight percentages of vinyl monomer units and polysiloxane-containing macromonomer units:
   a. from about 50% to about 98%, by weight of said copolymer, of vinyl monomer units, and
   b. from about 2% to about 50%, by weight of said copolymer, of polysiloxane-containing macromonomer units, wherein said polysiloxane-containing macromonomer units have a weight average molecular weight from about 1,000 to about 50,000, and correspond to the chemical formula:

$$X(Y)_n Si(R)_{3-m}(Z)_m$$

wherein:
   X is a vinyl group copolymerizable with said vinyl monomer units;
   Y is a divalent linking group;
   R is selected from the group consisting of hydrogen, hydroxyl, C1–C6 alkyl, C1–C6 alkoxy, C2–C6 alkylamino, phenyl, C1–C6 alky or alkoxy-substituted phenyl;
   Z is a monovalent siloxane polymeric moiety having a number average molecular weight of at least about 1000, is essentially unreactive under copolymerization conditions, and is pendant from said vinyl polymeric backbone after polymerization;
   n is 0 or 1; and
   m is an integer from 1 to 3.

8. A composition according to claim 7 wherein said vinyl monomer units are selected from the group consisting of acrylic acid, methacrylic acid, styrene, t-butylstyrene, t-butyl acrylate, 2-ethylhexyl methacrylate, n-butylacrylate, 2-methoxyethyl acrylate, isobutylene, n-propylmethacrylate, salts of any acids listed above, and combinations thereof.

9. A composition according to claim 7 wherein said polysiloxane-containing macromonomer units are selected from the group consisting of:

and wherein s is 0, 1, 2, 3, 4, 5 or 6; m is 1, 2 or 3; p is 0; q is 2, 3, 4, 5 or 6; $R^1$ is selected from the group consisting of hydrogen, hydroxyl, C1–C6 alkyl, C1–C6 alkoxy, C2–C6 alkylamino, phenyl, C1–C6 alkyl or alkoxy-substituted phenyl, $R^2$ is selected from the group consisting of C1–C6 alkyl or C1–C6 alkyl substituted phenyl; n is 0, 1, 2, 3 or 4; X is wherein $R^3$ is hydrogen or —COOH; $R^4$ is hydrogen, methyl or —CH$_2$COOH; Z is $R^5$, $R^6$, and $R^7$ independently are independently selected from the group consisting of hydrogen, hydroxyl, C1–C6 alkyl, C1–C6 alkoxy, C2–C6 alkylamino, phenyl, C1–C6 alkyl or alkoxy-substituted phenyl, and r is an integer of from about 14 to about 700.

10. A composition according to claim 9 wherein said polysiloxane-containing macromonomer units correspond to the chemical formula:

wherein m is 1; p is 0; q is 3; $R^1$ is methyl; X is wherein $R^3$ is hydrogen; $R^4$ is methyl; and Z is $R^5$, $R^6$, and $R^7$ are independently selected from the group consisting of hydrogen, hydroxyl, C1–C6 alkyl, C1–C6 alkoxy, C2–C6 alkylamino, phenyl, C1–C6 alkyl or alkoxy-substituted phenyl, and r is an integer of from about 14 to about 700.

11. A composition according to claim 10 wherein said copolymer comprises from about 0.1% to about 30%, by weight, of said composition.

12. A composition according to claim 5 wherein said copolymer is a silicone block copolymer.

13. A composition according to claim 12 wherein said silicone block copolymer corresponds to structures selected from the group consisting of A-B, A-B-A, and -(A-B)$_n$- and wherein said copolymer is formed from the random copolymerization of the following relative weight percentages of A vinyl monomer units and B siloxane units:
   a. from about 2% to about 50%, by weight of said copolymer of A siloxane units, and
   b. from about 50% to about 98%, by weight of said copolymer, of B vinyl monomer units,
wherein n is an integer of 2 or greater.

14. A composition according to claim 13 wherein said vinyl monomer units are selected from the group consisting of acrylic acid, methacrylic acid, styrene, t-butylstyrene, t-butyl acrylate, 2-ethylhexyl methacrylate, n-butylacrylate, 2-methoxyethyl acrylate, isobutylene, n-propylmethtacrylate, salts of any acids listed above, and combinations thereof.

15. A composition according to claim 14 wherein the silicone block portion, A, is represented by the following polymeric structure wherein each R is independently selected from the group consisting of hydrogen, hydroxyl, C1–C6 alkyl, C1–C6 alkoxy, C2–C6 alkylamino, styryl, phenyl, C1–C6 alkyl or alkoxy-substituted phenyl, and m is an integer of about 14 or greater.

16. A hair spray composition comprising a composition as in claim 1 which is dispensed from a mechanical spray pump.

17. A hair spray composition according to claim 2 wherein said composition further comprises a propellant.

18. A hair spray composition comprising a composition as in claim 17 which is dispensed from a pressurized aerosol canister.

19. A hair spray composition which after drying comprising: a silicone-containing adhesive copolymer containing one or more alkyl or aryl siloxane moieties, having a weight average molecular weight from about 10,000 to about 5,000,000, selected from the group consisting of:

(i) poly[(t-butylacrylate-co-n-butylacrylate-co-acrylic acid)-graft-poly(dimethylsiloxane)], (ii) poly[(t-butylacrylate-co-2-methoxyethyl acrylate-co-acrylic acid)-graft-poly(dimethylsiloxane)], (iii) poly(t-butylacrylate-co-acrylic acid)-graft-[poly(isobutylene); poly(dimethylsiloxane)];

(iv) poly(4-t-butylstyrene-co-methacrylic acid)-graft-[(poly(isobutylene); poly(dimethysiloxane)];

(v) poly[(t-butylstyrene-co-methacrylic acid)]-graft-[poly(2-ethylhexyl methacrylate), poly(dimethylsiloxane)], (vi) poly[(t-butylacrylate-co-2-methoxyethyl acrylate-co-methacrylic acid)]-graft[poly(n-propyl methacrylate-co-methacrylic acid); poly(dimethylsiloxane)], (vii) poly[(t-butylacrylate-co-2-methoxyethyl acrylate-co-methacrylic acid)]-graft-poly(n-propyl methacrylate-co-acrylic acid); poly(dimethylsiloxane)], (viii) poly[(t-butylacrylate-co-2-methoxyethyl acrylate-co-methacrylic acid)]-graft-[poly(stryene-co-methacrylic acid); poly(dimethylsiloxane)], (ix) [poly(dimethyl siloxane)-block-poly(t-butylacrylate-co-n-butylacrylate-co-acrylic acid-co-methacrylic acid)]$_n$, wherein n=an integer of 2 or greater, (x) [poly(dimethyl siloxane)-block-poly(t-butylacrylate-co-n-butylacrylate-co-acrylic acid-co-methacrylic acid)-block-poly(dimethyl siloxane)], (xi) poly(dimethyl siloxane)-block-poly(t-butylacrylate-co-n-butylacrylate-co-acrylic acid-co-methacrylic acid)

(xii) poly(t-butylacrylate-co-2-methoxyethylacrylate-co-acrylic acid)-graft-[poly(n-propyl methacrylate-co-methacrylic acid);poly(dimethylsiloxane)]

(xiii) poly(t-butylacrylate-co-n-butylacrylate-co-methacrylic acid-co-acrylic acid)-graft-poly(dimethylsiloxane)

(xiv) poly[(t-butylacrylate-co-2-methoxyethyl acrylate-co-acrylic acid)-graft-[poly(isobutylene);poly(dimethylsiloxane)]

(xv) and mixtures thereof;

has a cohesive strength of greater than about 0.5 kgf/mm$^2$ and a total energy absorption per unit volume of greater than about 0.55 kgfmm/mm$^3$.

20. A method of styling hair comprising the step of applying to the hair an effective amount of a composition according to claim 1.

21. A method of holding hair comprising the step of applying to the hair an effective amount of a composition according to claim 1.

22. A composition according to claim 1 wherein the composition is a hairspray composition which provides a hair stiffness value of from 0 to about 3.5 and a hair flaking value of from 0 to 3.5.

23. A composition according to claim 22 wherein the hair spray composition provides a hair stiffness value of from 0 to about 2.5 and a hair flaking value of from 0 to 2.5.

24. A composition according to claim 23 wherein the hair spray composition provides has a hair stiffness value of from 0 to about 2.0 and a hair flaking value of from 0 to about 2.0.

* * * * *

UNITED STATES PATENT AND TRADEMARK OFFICE
CERTIFICATE OF CORRECTION

PATENT NO.     : 6,113,883
DATED          : September 5, 2000
INVENTOR(S)    : Midha et al.

It is certified that error appears in the above-identified patent and that said Letters Patent is hereby corrected as shown below:

Column 4,
Line 20, "($\leqq 25°$ C.)" should read -- ($\leq 25°$ C) --.

Column 20,
Line 37, "about2:1" should read -- about 2:1 --.
Line 38, "about25:1" should read -- about 25:1 --.

Column 22,
Line 45, "liquefiable" should read -- liquifiable --.

Column 23,
Line 44, "fuirther" should read -- further --.

Column 27,
Line 48, "5,000,000" should read -- 5,000,000, --.

Column 31,
Line 2, "n-propylmethtacrylate" should read -- n-propylmethacrylate --.

Signed and Sealed this

Eighteenth Day of November, 2003

JAMES E. ROGAN
*Director of the United States Patent and Trademark Office*